United States Patent
Teramura (10) Patent No.: US 7,857,758 B2
(45) Date of Patent: Dec. 28, 2010

(54) OPTICAL PROBE AND OPTICAL TOMOGRAPHY SYSTEM

(75) Inventor: Yuichi Teramura, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 1101 days.

(21) Appl. No.: 11/540,643

(22) Filed: Oct. 2, 2006

(65) Prior Publication Data

US 2007/0078305 A1 Apr. 5, 2007

(30) Foreign Application Priority Data

Sep. 30, 2005 (JP) ............................. 2005-289178

(51) Int. Cl.
*A61B 1/06* (2006.01)
*A61B 1/07* (2006.01)

(52) U.S. Cl. .................... 600/182; 600/130; 359/200.1; 359/226.2; 250/227.26

(58) Field of Classification Search ................. 600/182, 600/137, 130; 359/200.1, 203.1, 210.2, 211.5, 359/220.1, 221.3, 226.2; 250/227.26, 234, 250/236
See application file for complete search history.

(56) References Cited

U.S. PATENT DOCUMENTS

| | | | |
|---|---|---|---|
| 6,294,775 B1 * | 9/2001 | Seibel et al. ............. | 250/208.1 |
| 6,546,272 B1 * | 4/2003 | MacKinnon et al. ........ | 600/407 |
| 6,564,087 B1 | 5/2003 | Pitris et al. | |
| 6,882,429 B1 * | 4/2005 | Weitekamp et al. ......... | 356/482 |
| 7,364,543 B2 * | 4/2008 | Yang et al. ................... | 600/173 |
| 7,544,162 B2 * | 6/2009 | Ohkubo ...................... | 600/173 |
| 7,577,471 B2 * | 8/2009 | Camus et al. ............... | 600/407 |
| 2003/0125630 A1 * | 7/2003 | Furnish ...................... | 600/461 |

FOREIGN PATENT DOCUMENTS

| | | |
|---|---|---|
| JP | 3-104984 A | 5/1991 |
| JP | 6-165784 A | 6/1994 |
| JP | 11-56786 A | 3/1999 |
| JP | 11056786 | 3/1999 |
| JP | 2000-321034 A | 11/2000 |
| JP | 2002214127 A | 7/2002 |
| JP | 2003-139688 A | 5/2003 |
| WO | 97/32182 A1 | 9/1997 |

* cited by examiner

*Primary Examiner*—John P Leubecker
*Assistant Examiner*—Jeffrey H Chang
(74) *Attorney, Agent, or Firm*—Sughrue Mion, PLLC (57) ABSTRACT

A support member and an optical fiber are disposed side by side inside a tubular outer envelope of an optical probe to extend in the longitudinal direction of the outer envelope. A light deflectors which deflects light emitted from the front end of the optical fiber in the circumferential direction of the outer envelope is provided and the light deflector is rotated in response rotation of the support member by a drive means such as a motor, whereby an optical probe which can deflect light emitted from the circumferential surface of the outer envelope in the circumferential direction of the outer envelope and is easy to make thinner and down its cost can be obtained.

10 Claims, 8 Drawing Sheets

OPTICAL PROBE AND OPTICAL TOMOGRAPHY SYSTEM

BACKGROUND OF THE INVENTION

1. Field of the Invention

This invention relates to an optical probe, and more particularly to an optical probe having a tubular outer envelope and having a function of deflecting light emitted from the peripheral surface thereof in the direction of circumference or the axis of the outer envelope. The present invention also relates to an optical tomography system where such an optical probe is employed.

2. Description of the Related Art

As a conventional method for obtaining tomographic images of measurement targets, such as living tissue, a method that obtains optical tomographic images by OCT (Optical Coherence Tomography) measurement has been proposed (refer to Japanese Unexamined Patent Publication Nos. 6(1994)-165784 and 2003-139688). The OCT measurement is a type of light interference measurement method that utilizes the fact that light interference is detected only when the optical path lengths of divided light beams, that is, a measurement light beam and a reference light beam, match within a range of coherence length of a light source. That is, in this method, a low coherent light beam emitted from a light source is divided into a measuring light beam and a reference light beam, the measuring light beam is irradiated onto a measurement target, and the measurement light beam reflected by the measurement target is led to a multiplexing means. Whereas the reference light beam is led to the multiplexing means after its optical path length is adjusted so that its optical path length equalizes to that of the reflected light from an arbitrary position in the object. Then the measuring light and the reference light is multiplexed by the multiplexing means, and the intensities thereof are detected by the light detector.

In order to obtain a one-dimensional tomographic image, an interference strength waveform according to the reflectance distribution along the same axis as the direction of travel of the measuring light by scanning the optical path length of the measuring light according to the measuring area. That is, a reflected light intensity distribution according to the structure in the direction of depth of the object to be measured can be obtained. Further, when the projecting position of the measuring light applied to the object is one-dimensionally scanned in a direction perpendicular to the optical axis by the use of a deflecting means or a physical means, a two dimensional tomography representing a reflected light intensity distribution can be obtained. Further, when the projecting position of the measuring light is two-dimensionally scanned in directions perpendicular to the optical axis, a three dimensional tomography representing a reflected light intensity distribution can be obtained.

In the above OCT system, a tomographic image is obtained by changing the optical path length of the reference light, thereby changing the measuring position (the depth of measurement) in the object. This technique is generally referred to as "TD-OCT (time domain OCT)". More specifically, in the optical path length changing mechanism for the reference light disclosed in Japanese Unexamined Patent Publication No. 6(1994)-165784, an optical system which collects the reference light emitted from the optical fiber on a mirror is provided and the optical path length is adjusted by moving only the mirror in the direction of the optical axis of the reference light. Further, in the optical path length changing mechanism for the reference light disclosed in Japanese Unexamined Patent Publication No. 2003-139688, the reference light emitted from the optical fiber is turned to parallel light by a lens, the reference light in the form of parallel light is collected and caused to enter the optical fiber again by an optical path length adjusting lens, and the optical path length adjusting lens is moved back and forth in the direction of the beam axis of the reference light.

Whereas, as a system for rapidly obtaining a tomographic image without changing the optical path length of the reference light, there has been proposed an optical tomography system for obtaining an optical tomographic image by measurement of SD-OCT (spectral domain OCT). In the SD-OCT system, a tomographic image which is one-dimensional in the optical axis is formed without physically scanning the optical path length, by dividing broad band, low coherent light into measuring light and reference light by the use of an interferometer as in the above-described TD-OCT system, substantially equalizing the measuring light and the reference light to cause them to interfere with each other, decomposing the interference light into the optical frequency components, measuring the intensity of the interference light by the optical frequency components by an array type detector and carrying out a Fourier analysis on the obtained spectral interference waveforms by a computer. As in above-described TD-OCT system, a two-dimensional or a three-dimensional can be obtained by scanning the projecting position of the measuring light in directions perpendicular to the optical axis.

As another system for rapidly obtaining a tomographic image without changing the optical path length of the reference light, there has been proposed an optical tomography system for obtaining an optical tomographic image by measurement of SS-OCT (swept source OCT). The SS-OCT system employs a light frequency tunable laser as a light source. The high coherence laser beam is divided into measuring light and reference light. The measuring light is projected onto the object and the reflected light from the object is led to the multiplexing means. The reference light is led to the multiplexing means after it is made substantially equal to the measuring light in the optical path length to cause the measuring light and the reference light to interfere with each other, and the measuring light and the reference light are multiplexed by the multiplexing means. The intensity of the multiplexed light is detected by an optical detector. The intensity of the interference light is measured by the frequency component by sweeping the frequency of the light frequency tunable laser and a one-dimensional tomography in the optical axis is formed without physically scanning the optical path length by Fourier-transforming the spectral interference waveform thus obtained with a computer. As in above-described TD-OCT system, a two-dimensional or a three-dimensional can be obtained by scanning the projecting position of the measuring light in directions perpendicular to the optical axis.

In the optical tomography system of each of the systems described above, a tomographic image along a certain surface of the object is generally obtained and for this purpose, it is necessary to at least one-dimensionally scan the measuring light beam in the object. As a means for effecting such a light scanning, there has been known, as disclosed in Japanese Patent No. 3104984, an optical probe having a tubular outer envelope and having a function of deflecting light emitted from the peripheral surface thereof in the direction of circumference of the outer envelope. More specifically, the optical probe comprises an inserting portion (outer envelope) which is inserted into the sample, a rotatable hollow shaft which is inserted inside the outer envelope, an optical fiber which is passed through the shaft, and a light deflecting element which is connected to the leading end portion of the shaft to be rotated together therewith and deflects light radiated from the leading end portion of the optical fiber in a direction of circumference of the outer envelope.

Observing an optical tomographic image has been expected to be developed from the digestive organ which has been reported in the past to a finer region such as a bronchus, a ureter, and a blood vessel. From such a viewpoint, it has been required to make thinner the optical probe. However, in the optical probe disclosed in Japanese Patent No. 3104984, it is necessary to have a certain wall thickness to ensure the strength of the shaft and to ensure a space between the shaft and the optical fiber inside thereof, which makes difficult to make thinner the optical probe.

There is a further demand that a deeper region of the object is to be observed. However, to realize this, it is necessary to make a probe as long as several meters, and it is very difficult to pass an optical fiber through the inside of a shaft which is cylindrical and elongated. Further, the optical fiber can be damaged when it is passed through the inside of such a shaft and accordingly, use of such a probe deteriorates the productivity. Further, since such a cylindrical shaft is high in its manufacturing cost, the optical probe is high in cost.

SUMMARY OF THE INVENTION

In view of the foregoing observations and description, the primary object of the present invention is to provide an optical probe which is easy to make thin and can be produced at low cost.

Another object of the present invention is to provide an optical tomography system which can be miniaturized and can be manufactured at low cost by the use of such an optical probe.

In accordance with the present invention, the above objects are accomplished by avoiding a complicated structure of passing a hollow shaft through the outer envelope of the optical probe and passing an optical fiber through the shaft and disposing in the outer envelope a support member for rotating a light deflecting element with the optical fiber side by side.

In accordance with the present invention, there is provided an optical probe comprising a tubular outer envelope, a support member which extends in the longitudinal direction of the outer envelope inside the outer envelope, an optical fiber which extends side by side together with the support member inside the outer envelope, a drive means which is connected to the base end portion of the support member and rotates the support member in the circumferential direction of the outer envelope, a light deflecting element which is rotated together with the support member and deflects light emitted from an end of the optical fiber in the circumferential direction of the outer envelope, a light collecting means which collects light emitted from an end of the optical fiber and converges it on a body-to-be-scanned disposed externally of the circumference of the outer envelope, and a light guide means which guides light reflected by the body-to-be-scanned to an end of the optical fiber to enter the optical fiber from the end.

It is preferred in the optical probe of the present invention that the support member and the optical fiber be integrated so that the optical fiber rotates together with the support member.

In this case, it is preferred that the optical fiber be supported by the support member so that its central axis is deviated from the center of rotation of the support member, and a bearing portion which bears for rotation the rotating shaft of the support member be disposed in an end of the outer envelope.

The tomography system of the present invention is characterized in that the optical probe of the present invention is employed in each of the above described various systems of the optical tomography systems. That is, in accordance with the present invention, there is provided an optical tomography system for obtaining a tomographic image of an object to be measured comprising a light unit source which emits light, a light dividing means which divides light emitted from the light source unit into measuring light and reference light, a projecting optical system which projects the measuring light onto the object, a multiplexing means which multiplexes the reflected light from the object when the measuring light is projected onto the object and the reference light, an interference light detecting means which detects interference light of the reflected light and the reference light which have been multiplexed by the multiplexing means, and a tomographic image obtaining means which detects intensities of the interference light in positions in the direction of depth of the object on the basis of the frequency and intensity of the detected interference light and obtains a tomographic image of the object on the basis of the intensity of the reflected light in each position of the depth, wherein the improvement comprises that the projecting optical system includes an optical probe of the present invention.

The optical probe in accordance with the present invention, where a support member and an optical fiber are disposed side by side in the outer envelope of the probe and the support member is rotated to rotate the light deflecting element, can be very simpler in structure as compared with the conventional optical probe where a hollow shaft is passed through the outer envelope of the probe and an optical fiber is passed through the shaft. Accordingly, the optical probe of the present invention is easy to make thin and can be manufactured at low cost.

Further, since in the optical probe in accordance with the present invention, a support member and an optical fiber are disposed side by side in the outer envelope of the probe, combination and fixture of the support member and the optical fiber cannot be very difficult. Accordingly, the manufacturing cost can be low.

Especially, when the optical fiber is supported by the support member so that its central axis is deviated from the center of rotation of the support member, and a bearing portion which bears for rotation the rotating shaft of the support member be disposed in an end of the outer envelope, the probe diameter can be smaller by rotating the optical fiber about a rotating axis deviated from the center of rotation of the optical fiber in the outer envelope.

Further, since the optical probe of the present invention is applied, the optical tomography system of the present invention can be miniaturized and can be manufactured at low cost.

DESCRIPTION OF THE PREFERRED EMBODIMENTS

Figure 1:
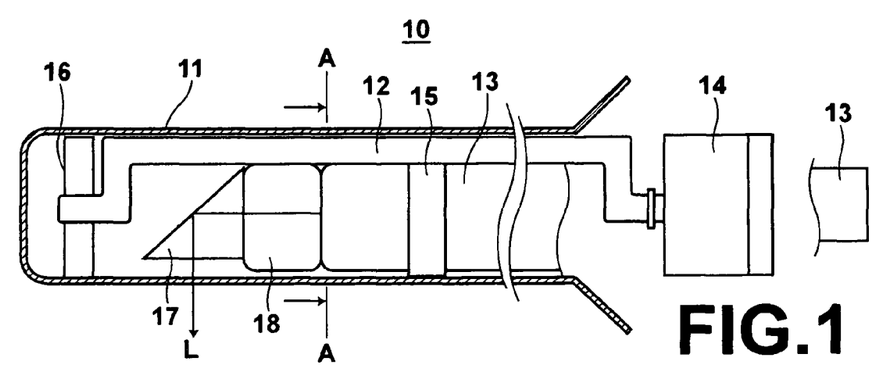
FIG. 1 is a side cross-sectional view showing an optical probe in accordance with a first embodiment of the present invention.
Figure 2:
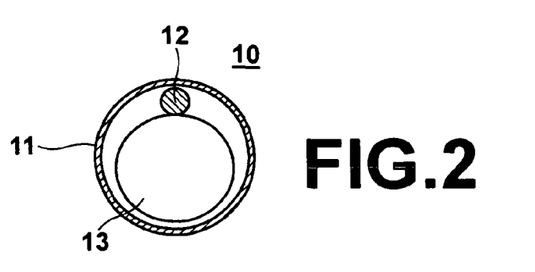
FIG. 2 is a front cross-sectional view of the optical probe of FIG. 1.
Figure 3:
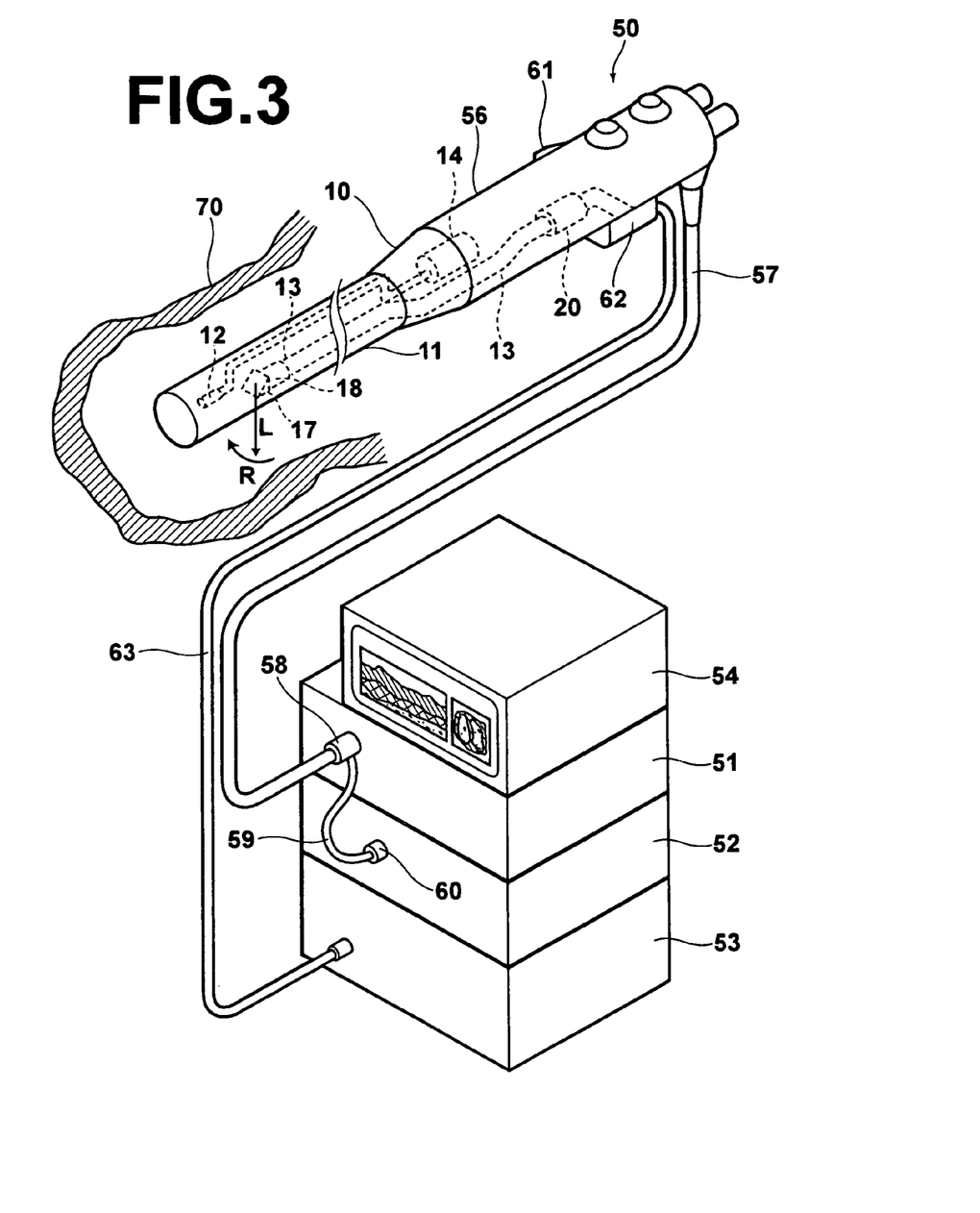
FIG. 3 is a perspective view of an optical tomographic system to which the optical probe of FIG. 1 is applied.

Embodiments of the present invention will be described in detail with reference to the drawings, hereinbelow. FIG. 1 shows a side cross-sectional shape of an optical probe 10 in accordance with a first embodiment of the present invention and FIG. 2 is a front cross-sectional view of the optical probe 10 taken along line A-A in FIG. 1. For example, the optical probe 10 forms a front end portion of an endoscope which forms a part of an optical tomography system. FIG. 3 shows an entire shape of the optical tomography system.

The optical tomography system will be first described in brief with reference to FIG. 3. The system comprises an endoscope 50 including the optical probe 10; a light source unit 51 a video processor 52, and an optical tomographic processing system 53 to which the endoscope 50 is connected; and a monitor 54 connected to the video processor 52. The endoscope 50 comprises an outer envelope 11 which is flexible and elongated, a control portion 56 connected to the rear end of the endoscope outer envelope 11 and a universal code 57 which extends outward from a side portion of the control portion 56.

A light guide (not shown) which transmits illuminating light from the light source unit 51 is passed through the universal code 57, and a light source connector 58 which is removably connected to the light source unit 51 is provided on the end of the universal code 57. A signal cable 59 extends from the light source connector 58 and a signal connector 60 which is removably connected to the video processor 52 is provided on the end of the signal cable 59. The light source unit 51 is for projecting the illuminating light onto a part of a sample 70 a tomographic image of which is to be obtained as described later.

A bight control knob 61 for controlling a bight portion provided in the probe outer envelope 11 and a light guide drive portion 62 are provided on the control portion 56, and the light guide drive portion 62 and the optical tomographic processing system 53 are connected to each other by way of a light guide 63. The probe outer envelope 11 is inserted into the sample 70 such as a human organ.

The optical probe 10 will be described with reference to FIGS. 1 and 2, hereinbelow. The optical probe 10 comprises: a cylindrical probe outer envelope 11 having a closed front end; a support member 12 disposed inside the outer envelope 11 to extend in the direction of axis of the outer envelope 11; a single optical fiber 13, which is provided inside the outer envelope 11 to extend side by side with the support member 12; and a motor 14 which is connected to the support member 12 in a position toward the base end thereof and rotates the support member 12 in the circumferential direction of the probe outer envelope 11.

The optical fiber 13 is fixed to the support member 12 by a fiber fixing member 15. A disk-like bearing 16 having a through hole at the center thereof is fixed to the outer probe 11 near the front end thereof. The front end portion of the support member 12 is L-shaped, and the support member 12 is rotatable about the central axis (longitudinal axis) of the probe outer envelope 11 by inserting the front end portion of the support member 12 into the through hole of the bearing 16. Accordingly, when the motor 14 is driven, the support member 12 rotates together with the optical fiber 13.

The optical probe 10 is further provided with a prism mirror 17 which is supported by the support member 12 to rotate together with the support member 12 to deflect light L emitted from the front end of the optical fiber 13 in the circumferential direction of the probe outer envelope 11, and a rod lens 18 which collects light L emitted from the front end of the optical fiber 13 to converge on the sample 70 as the object to be scanned which is disposed externally of the circumference of the outer envelope 11. In this particular embodiment, the rod lens 18 and the prism mirror 17 double as a light-guide means which leads the light L reflected by the sample 70 to the front end of the optical fiber 13 to enter the optical fiber 13 from the front end as will be described later.

The part of the optical fiber 13 near the base end thereof is bent to bypass the motor 14 and the base end is disposed coaxially with the rotating axis of the support member 12. An incident optical system 20 is disposed inside the endoscope 50 to be opposed to the base end of the optical fiber 13 as shown in FIG. 3. Light L propagating the light guide 63 and emitted from the light guide 63 is collected by the incident optical system 20 and enters the optical fiber 13 from the base end thereof.

Operation of the optical probe 10 will be described, hereinbelow. A light source such as a laser (not shown) is disposed in the optical tomographic processing system 53 shown FIG. 3, and the light L such as a laser beam emitted therefrom enters the light guide 63 and propagates therethrough. The light L entering the optical fiber 13 by way of the incident optical system 20 after emitted from the light guide 63 propagates through the optical fiber 13, is emitted from the front end thereof, is reflected by 90° by the prism mirror after collected by the rod lens 18 and is emitted outside the probe 10 through the outer envelope 11 which is light-transmittable. Then when the motor 14 is driven, the support member 12 rotates as described above and the optical fiber 13, prism mirror 17 and the rod lens 18 fixed thereto are rotated together with the support member 12.

In response to rotation of the prism mirror 17, the light L emitted therefrom is deflected in the circumferential direction of the probe outer envelope 11, thereby scanning the sample 70 in the direction of arrow R in FIG. 3. The light L is reflected by the sample 70 while scattering and a part of the reflected light impinges upon the prism mirror 17 and is reflected toward the rod lens 18. The part of the reflected light is collected by the rod lens 18 and enters the optical fiber 13 from the front end thereof.

The reflected light thus propagating through the optical fiber 13 is emitted from the base end of the optical fiber 13, enters the light guide 63 by way of the incident optical system 20, and propagates through the light guide 63 to be transmitted to the optical tomographic processing system 53. In the optical tomographic processing system 53, the above described reflected light is branched from the optical path of the light L to the optical probe 10, and is detected by an optical detector (not shown). A tomographic image of the sample 70 is formed on the basis of the output of the optical detector and the tomographic image is displayed on the monitor 54 shown in FIG. 3.

As can be understood from the description above, the optical probe 10 of this embodiment, where the support member 12 and the optical fiber 13 are disposed side by side in the probe outer envelope 11 and the support member 12 is rotated to rotate the prism mirror 17 as the light deflecting element, can be very simpler in structure as compared with the conventional optical probe where a hollow shaft is passed through the outer envelope of the probe and an optical fiber is passed through the shaft. Accordingly, the optical probe 10 is easy to make thin and can be manufactured at low cost.

Further, since in the optical probe 10 of this embodiment, a support member 12 and an optical fiber 13 are disposed side by side in the outer envelope 11 of the probe 13, combination and fixture of the support member 12 and the optical fiber 13 cannot be very difficult. Accordingly, the manufacturing cost can be low.

In this embodiment, since the optical fiber 13 is supported by the support member 12 so that its central axis is deviated from the center of rotation of the support member, the optical fiber 13 rotates about a rotating axis deviated from the central axis of the optical fiber 13 in the probe outer envelope 11. In this case, as can be seen from FIG. 2, the inner diameter of the probe outer envelope 11 has only to ensure the outer diameter of the optical fiber 13 and the vertical dimension of the support member 12. Whereas, when the support member is tubular and the optical fiber coaxially disposed therein is rotated, the inner diameter of the probe outer envelope 11 must ensure the outer diameter of the optical fiber 13 and the vertical dimension of the support member ×2, whereby the probe outer envelope 11 must be thicker if the thickness of the tubular support member is the same as the above described vertical dimension.

Figure 4:
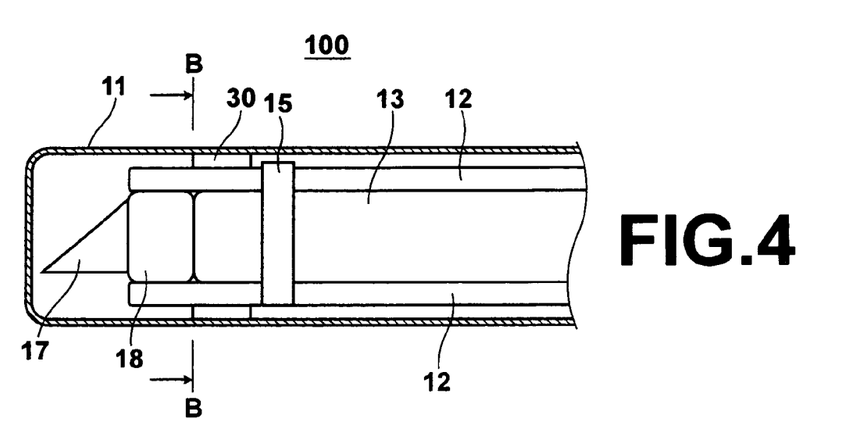
FIG. 4 is a side cross-sectional view showing an optical probe in accordance with a second embodiment of the present invention.
Figure 5:
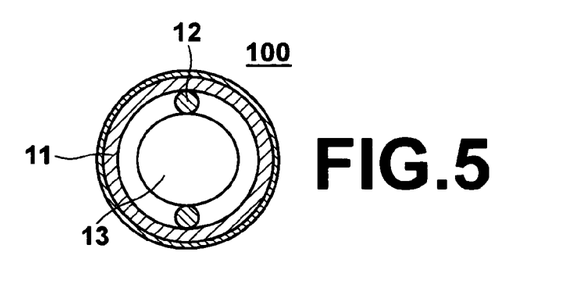
FIG. 5 is a front cross-sectional view of the optical probe of FIG. 4.

A second embodiment of the present invention will be described, hereinbelow. FIG. 4 is a side cross-sectional view of an optical probe 100 in accordance with the second embodiment of the present invention and FIG. 5 is a front cross-sectional view taken along line B-B in FIG. 4. In FIGS. 4 and 5, the elements analogous to those in FIGS. 1 to 3 are given the same reference numerals and will not be described unless necessary.

The optical probe 100 of the second embodiment differs from that 10 of the first embodiment in that a pair of support members 12 are provided with the optical fiber 13 interposed therebetween, and the support members 12 are supported for rotation in the annular bearing 30.

Figure 6:
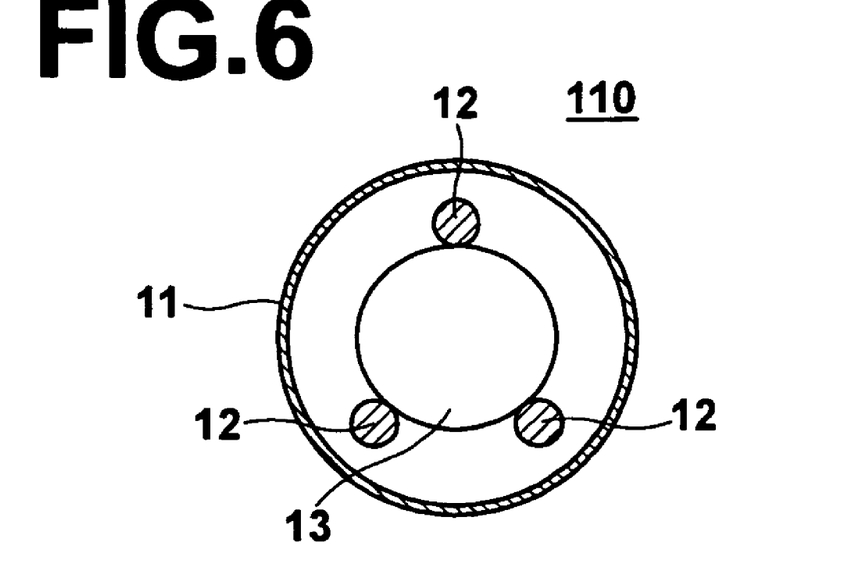
FIG. 6 is a front cross-sectional view showing an optical probe in accordance with a third embodiment of the present invention.

A third embodiment of the present invention will be described, hereinbelow. FIG. 6 is a front cross-sectional view of an optical probe 110 in accordance with the third embodiment of the present invention. The optical probe 110 of the third embodiment differs from that 10 of the first embodiment in that three support members 12 are provided with the optical fiber 13 interposed thereamong and no bearing supporting the support members 12 is provided. That is, the inner diameter of the probe outer envelope 11 is in such a dimension that a slight space is formed between the support members 12 and the probe outer envelope 11, and the support members 12 slide on the inner surface of the probe outer envelope 11 when they rotate.

Though not shown, the optical fiber 13 is fixed to the three support members 12 by a fiber fixing member the same as the fiber fixing member 15 shown in FIGS. 1 and 4. Though it is preferred that the three support members 12 be equiangularly disposed about the optical fiber 13, the three support members 12 may be not equiangularly disposed about the optical fiber 13.

Figure 7:
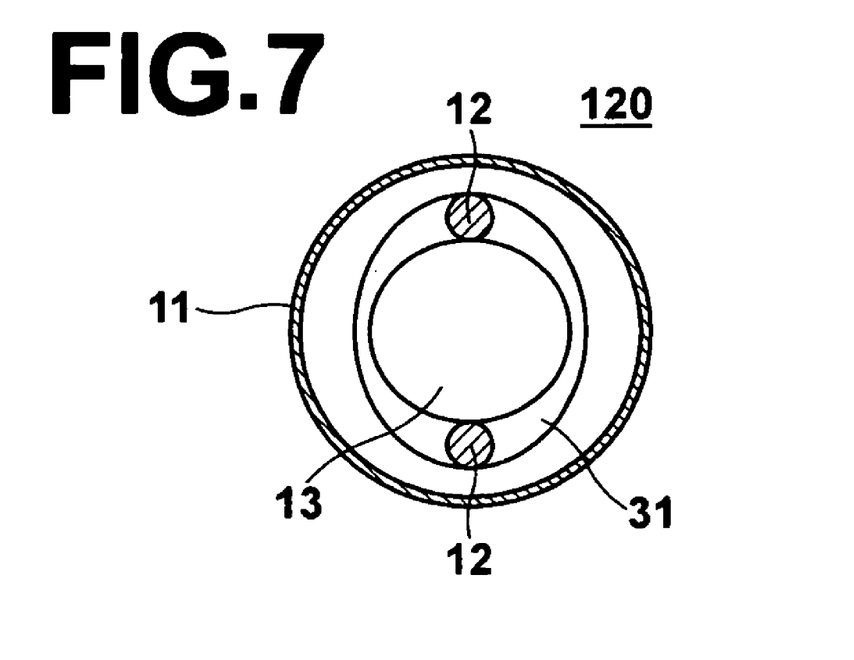
FIG. 7 is a front cross-sectional view showing an optical probe in accordance with a fourth embodiment of the present invention.

A fourth embodiment of the present invention will be described, hereinbelow. FIG. 7 is a front cross-sectional view of an optical probe 120 in accordance with the fourth embodiment of the present invention. The optical probe 120 of the fourth embodiment differs from that 110 of the third embodiment in that a pair of support members 12 are provided and the support members 12 are integrated with the optical fiber 13 by a coating member 31 extending substantially over the entire length. That is, the inner diameter of the probe outer envelope 11 is in such a dimension that a slight space is formed between the coating members 31 and the probe outer envelope 11, and the coating members 31 slide on the inner surface of the probe outer envelope 11 when they rotate.

Figure 8:
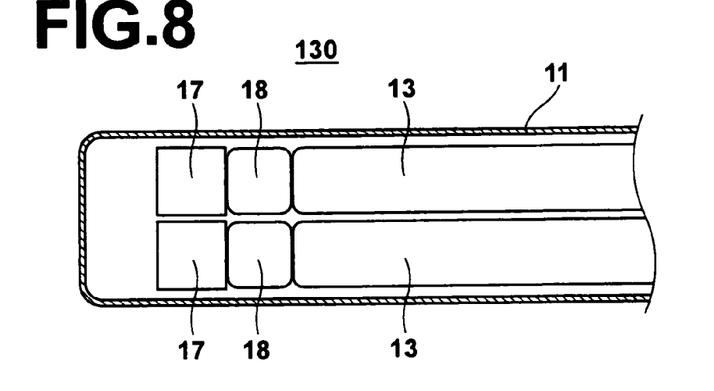
FIG. 8 is a side cross-sectional view showing an optical probe in accordance with a fifth embodiment of the present invention.
Figure 9:
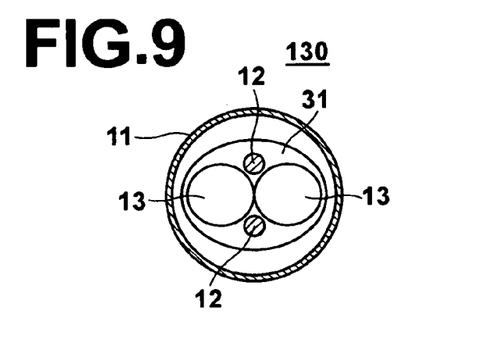
FIG. 9 is a front cross-sectional view of the optical probe of FIG. 8.

A fifth embodiment of the present invention will be described, hereinbelow. FIGS. 8 and 9 are respectively a side cross-sectional view and a front cross-sectional view of an optical probe 130 in accordance with the fifth embodiment of the present invention. The optical probe 130 of the fifth embodiment differs from that 120 of the fourth embodiment in that a pair of optical fibers 13 are provided. In response to provision of a pair of optical fibers 13, a pair of prism mirrors 17 and a pair of rod lenses 18 are provided. In FIG. 8, the coating member 31 shown in FIG. 9 is abbreviated.

In the optical probe 130 of this embodiment, one optical fiber 13 is exclusively sending light and the light emitted from the front end thereof is projected onto an object-to-be-scanned (e.g., the sample 70 shown in FIG. 3) by way of the corresponding rod lens 18 and the prism mirror 17. That is, in this case, light is emitted from a prism mirror 17 corresponding to said one optical fiber 13 in a direction perpendicular to the plane of paper in FIG. 8.

The light reflected by the object-to-be-scanned enters another prism mirror 17 and is reflected there to be collected by another rod lens 18 to enter another optical fiber 13 exclusively for receiving light. The light propagates said another optical fiber 13 and is sent to a predetermined light receiving portion.

Figure 10:
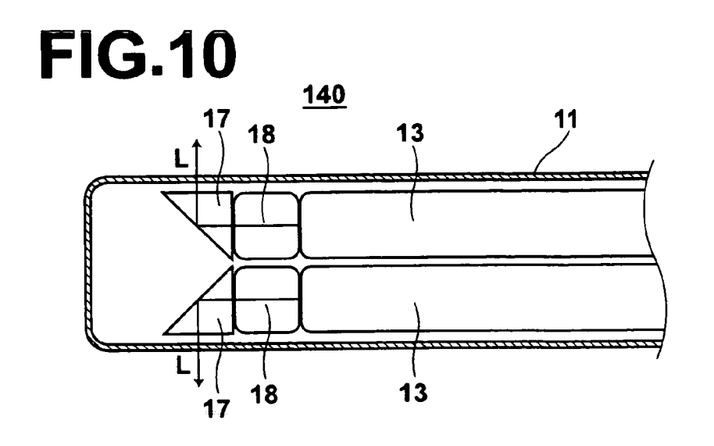
FIG. 10 is a side cross-sectional view showing an optical probe in accordance with a sixth embodiment of the present invention.

A sixth embodiment of the present invention will be described, hereinbelow. FIG. 10 is a side cross-sectional view of an optical probe 140 in accordance with the sixth embodiment of the present invention. The optical probe 140 of the sixth embodiment differs from that 130 of the fifth embodiment in that the pair of optical fibers 13 respectively double the light sending optical fiber and the light receiving optical fiber.

That is, in this embodiment, the pair of prism mirrors 17 are disposed with their orientations opposite to each other, and light L different from each other by 180° in the direction is emitted from the prism mirrors 17. The light L emitted from one optical fiber 13 and reflected by the object returns to said one optical fiber 13 and the light L emitted from the other optical fiber 13 and reflected by the object returns to said the other optical fiber 13. With this arrangement, it is possible to simultaneously scan different parts on the object or to scan the same part on the object at a higher speed.

Also in the second to sixth embodiments, since a single or a plurality of support members 12 and a single or a plurality of optical fibers 13 are basically disposed side by side in the probe outer envelope 11, and the support member(S) is rotated to rotate the prism mirror 17, a result similar to the first embodiment can be obtained.

Though each of the optical probes described above forms an endoscope which is a part of the optical tomography system, the present invention can be applied to various optical probes having a tubular outer envelope and having a function of deflecting light emitted from the peripheral surface thereof in the direction of circumference of the outer envelope without being limited to the optical probes of such a type.

Though in the embodiments described above, the light deflecting element, light collecting means and the optical fiber are in close contact with each other, it is not necessary but they may be spaced from each other. Positions of the light deflecting element and the light collecting means along the optical axis in the above embodiments may be reversed and the light deflecting element may be positioned on the side nearer to the light source.

Figure 11:
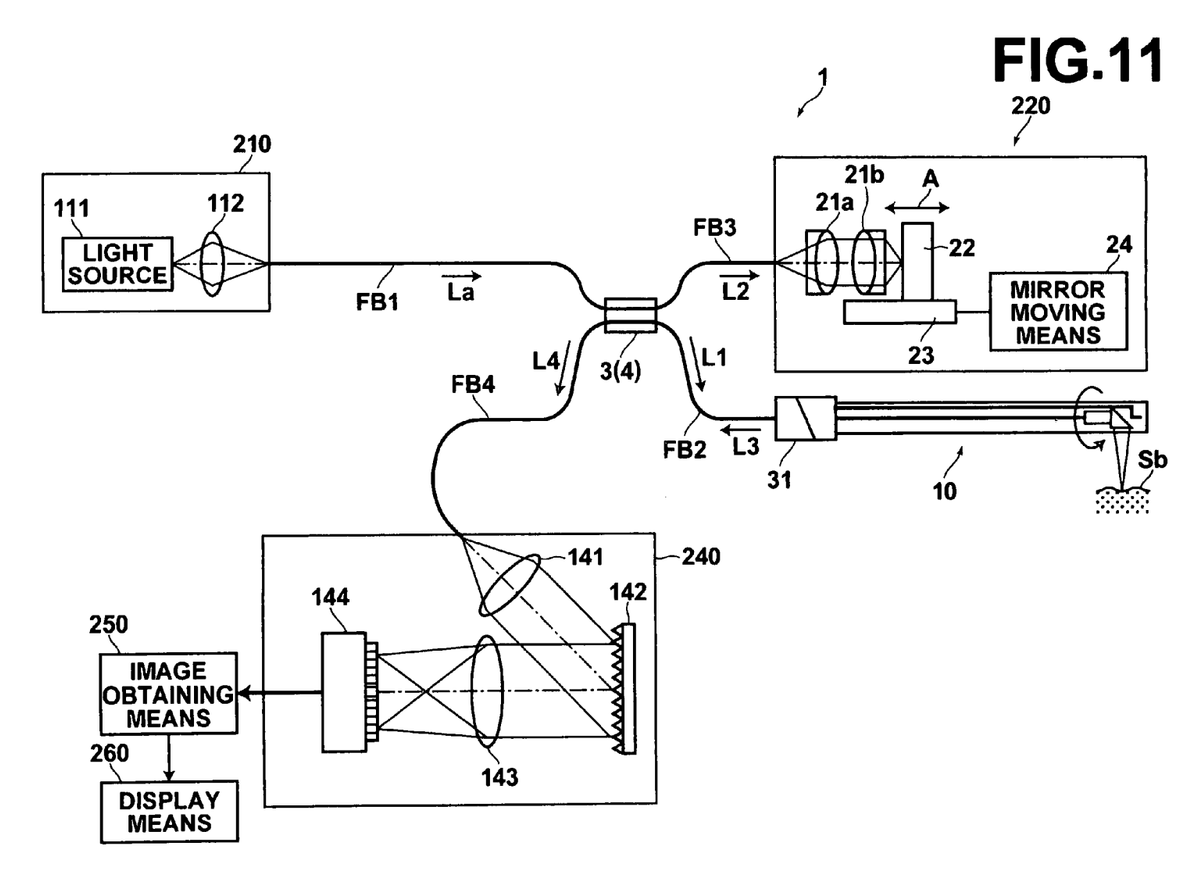
FIG. 11 is a schematic view showing an example of the optical tomography system by the SD-OCT measurement to which the optical probe of the present invention is applied.

Examples of the optical tomography system to which the optical probes of the present invention are to be applied will be described, hereinbelow. The optical tomography system 1 shown in FIG. 11 is for obtaining a tomographic image of an object of measurement such as a living tissue or a cell in a body cavity by measuring the SD-OCT. The optical tomography system 1 of this embodiment comprises: a light source unit 210 which emits light La; a light dividing means 3 which divides the light La emitted from the light source unit 210 into measuring light L1 and reference light L2; an optical path length adjusting means 220 which adjusts the optical path length of the reference light L2 divided by the light dividing means 3; an optical probe 10 which guides to the object Sb to be measured the measuring light beam L1 divided by the light dividing means 3; a multiplexing means 4 for multiplexing a reflected light beam L3 from the object Sb when the measuring light beam L1 is irradiated onto the object Sb from the probe 10, and the reference light beam L2; and an interference light detecting means 240 for detecting interference light beam L4 of the reflected light beam L3 and the reference light beam L2 which have been multiplexed by the multiplexing means 4.

The light source unit 210 comprises a light source 111 which emits low coherence light La such as an SLD (super luminescent diode), ASE (amplified spontaneous emission) or a super continium where an ultra short pulse laser beam is projected onto a nonlinear medium to obtain broad band light and an optical system 112 which enters the light emitted from the light source 111 into an optical fiber FB1.

The light dividing means 3 comprises, for instance, a 2×2 fiber optic coupler and divides the light beam La led thereto by way of the optical fiber FB1 from the light source unit 210 into the measuring light beam L1 and the reference light beam L2. The light dividing means 3 is optically connected to two optical fibers FB2 and FB3, and the measuring light beam L1 is propagated through the optical fiber FB2 while the reference light beam L2 is propagated through the optical fiber FB3. In this embodiment, the light dividing means 3 also functions as the multiplexing means 4.

The optical probe 10 previously shown in FIG. 1 is optically connected to the optical fiber FB2 and the measuring light beam L1 is guided to the probe 10 from the optical fiber FB2. The probe 10 is inserted into a body cavity, for instance, through a forceps port by way of a forceps channel and is removably mounted on the optical fiber FB2 by an optical connector 31.

The optical path length adjusting means 220 is disposed on the side of the optical fiber FB3 radiating the reference light beam L2. The optical path length adjusting means 220 changes the optical path length of the reference light beam L2 in order to adjust a range over which a tomographic image is to be obtained and comprises a reflecting mirror 22 which reflects the reference light beam L2 radiated from the optical fiber FB3, a first lens 21*a* disposed between the reflecting mirror 22 and the optical fiber FB3, and a second lens 21*b* disposed between the first lens 21*a* and the reflecting mirror 22.

The first lens 21*a* makes parallel the reference light beam L2 radiated from the core of the optical fiber FB3 and at the same time, collects the reference light beam L2 reflected by the reflecting mirror 2 on the core of the optical fiber FB3. The second lens 21*b* collects the reference light beam L2 made parallel by the first lens 21*a* on the reflecting mirror 22 and at the same time, makes parallel the reference light beam L2 reflected by the reflecting mirror 22. That is, the first and second lenses 21*a* and 21*b* form a confocal optical system.

Accordingly, the reference light beam L2 radiated from the optical fiber FB3 is turned to a parallel light by the first lens 21*a* and is collected on the reflecting mirror 22 by the second lens 21*b*. Subsequently, the reference light beam L2 reflected by the reflecting mirror 22 is turned to a parallel light by the second lens 21*b* and is collected on the core of the optical fiber FB3 by the first lens 21*a*.

The optical path length adjusting means 220 is further provided with a base portion 23 to which the second lens 21*b* and the reflecting mirror 22 are fixed and a mirror movement means 24 which moves the base portion 23 in the direction of the optical axis of the first lens 21*a*. In response to movement of the base portion 23 in the direction of arrow A, the optical path length of the reference light beam L2 can be changed.

The multiplexing means 4 comprises a 2×2 fiber optic coupler as described above, and multiplexes the reference light beam L2 which has been shifted in its frequency and has been changed in its optical path length by the optical path length adjusting means 220 and the reflected light beam L3 from the object S to emit the multiplexed light beam toward the interference light detecting means 240 by way of an optical fiber FB4.

The interference light detecting means 240 detects interference light L4 of the reflected light beam L3 and the reference light beam L2 which have been multiplexed by the multiplexing means, and comprises a collimator lens 141 which makes parallel the interference light beam L4 radiated from the optical fiber FB4, a spectral means 142 which divides the interference light beam L4 having a plurality of wavelength bands by the wavelength bands and a light detecting means 144 which detects each wavelength band of the interference light beam L4 divided by the spectral means 142.

The spectral means 142 comprises, for instance, a diffraction grating element, and spectrally divides the interference light beam L4 entering it to output the divided interference light beam L4 to the light detecting means 144. The light detecting means 144 is formed by, for instance, a CCD element which comprises a plurality of, for instance, one-dimensionally or two-dimensionally arranged photosensors and each of the photosensors detects each wavelength band of the interference light beam L4 spectrally divided as described above.

The light detecting means 144 is connected to an image obtaining means 250 comprising, for instance, a computer system such as a personal computer. The image obtaining means 250 is connected to a display system 260 formed, for instance, by a CRT or a liquid crystal display system.

Operation of the optical tomography system 1 having a structure described above will be described, hereinbelow. When a tomographic image is to be obtained, the optical path length is first adjusted by moving the base 23 in the direction of the arrow A so that the object Sb is positioned in the measurable area. The light beam La is emitted from the light source unit 210 and the light beam La is divided into the measuring light beam L1 and the reference light beam L2. The measuring light beam L1 is radiated from the optical probe 10 toward a body cavity and is projected onto the object Sb. At this time, the measuring light beam L1 radiated from the optical probe 10 is caused to one-dimensionally scan the object Sb by the optical probe 10 operating as described above. Then the reflected light beam L3 from the object Sb and the reference light beam L2 are multiplexed, and the interference light beam L4 of the reflected light beam L3 and the reference light beam L2 is detected by the interference light detecting means 240. Information on the intensity distribution of the reflected light in the direction of depth of the object Sb is obtained by carrying out frequency analysis on the detected interference light beam L4 in the image obtaining means 50 after carrying out a suitable waveform compensation and noise removal.

By causing the measuring light beam L1 to scan the object Sb by the optical probe 10 as described above, information on the direction of depth of the object Sb is obtained and accordingly tomographic images on the cross-section including the direction of scan can be obtained. The tomographic images thus obtained are displayed by the display system 260. Further, for instance, by moving the optical probe 10 right and left in FIG. 1 so that the measuring light L1 scans the object Sb in a second direction perpendicular to said direction of scan, tomographic images on the cross-section including the second direction can be obtained.

Figure 12:
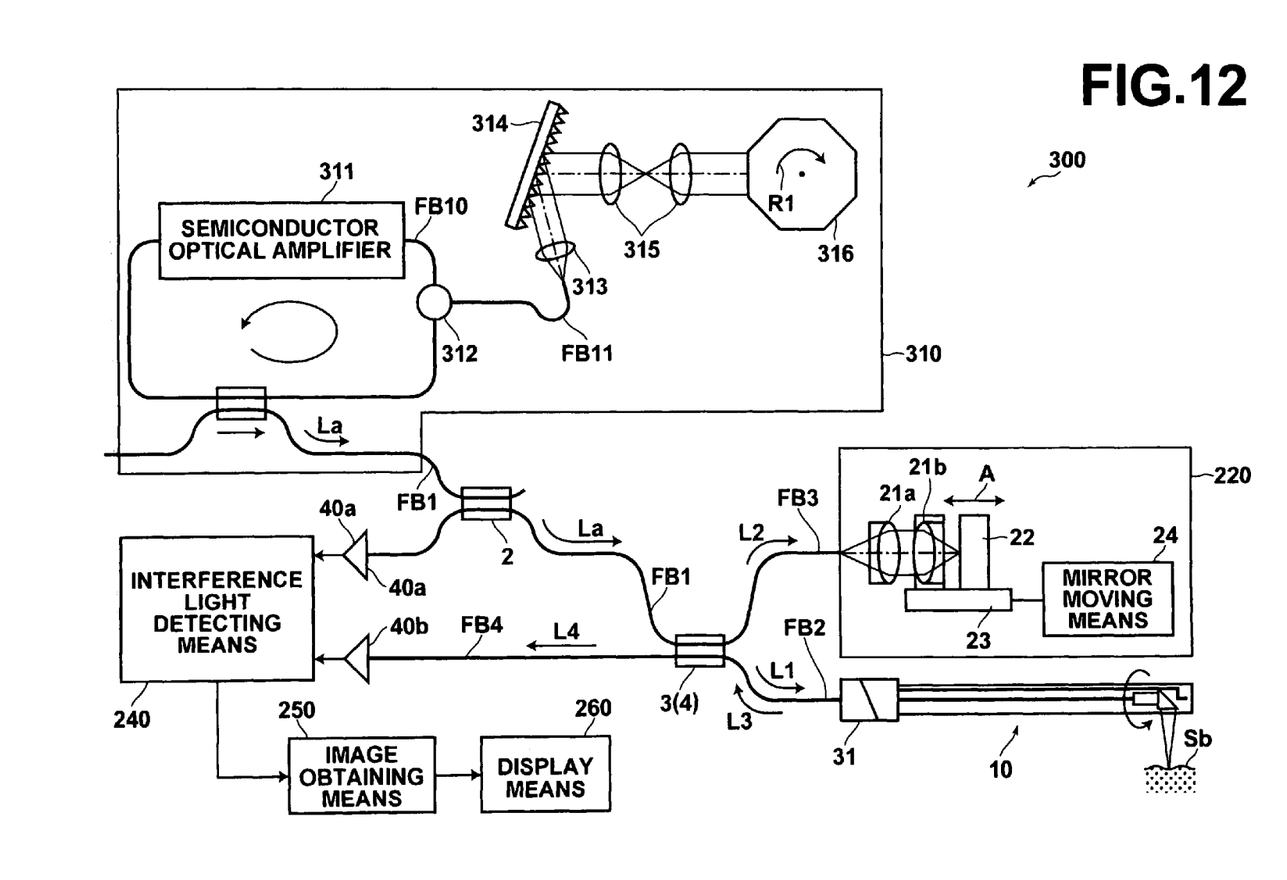
FIG. 12 is a schematic view showing an example of the optical tomography system by the SS-OCT measurement to which the optical probe of the present invention is applied.

Another example of the optical tomography system to which the optical probes of the present invention are to be applied will be described, hereinbelow. The optical tomography system 300 shown in FIG. 12 is for obtaining a tomographic image of the object of measurement by measuring the SS-OCT and specifically differs from the optical tomography system 1 shown in FIG. 11 in that structure of the light source unit and the interference light detecting means.

The light source unit 310 of this system emits a laser beam La while sweeping its wavelength at a predetermined period. Specifically, the light source unit 310 comprises a semiconductor optical amplifier (a semiconductor gain medium) 311 and an optical fiber FB10 connected to the semiconductor optical amplifier 311 at opposite ends thereof. The semiconductor optical amplifier 311 emits weak light to one end of the optical fiber FB10 in response to injection of a drive current and amplifies light input from the other end of the optical fiber FB10. When a drive current is supplied to the semiconductor optical amplifier 311, a pulse-like laser beam La is emitted to the optical fiber FB1 by a resonator formed by the semiconductor optical amplifier 311 and the optical fiber FB10.

Further, an optical divider 312 is connected to the optical fiber FB10 and a part of the light beam propagated through the optical fiber FB10 is emitted from the optical divider 312 toward the optical fiber FB11. Light emitted from the optical fiber FB11 travels through the collimator lens 313, the diffraction grating 314 and the optical system 315 and is reflected by the rotating polygon mirror 316. The reflected light is returned to the optical fiber FB11 by way of the optical system 315, the diffraction grating 314 and the collimator lens 313.

The rotating polygon mirror 316 rotates in the direction indicated by arrow R1, to vary the angle of each reflective surface thereof with respect to the optical axis of the optical system 315. Thereby, only a light beam having a specific frequency, from among the light spectrally split by the diffraction grating 314, is returned to the optical fiber FB11. The frequency of the light beam that reenters the optical fiber FB11 is determined by the angle formed by the optical axis of the optical system 315 and the reflective surface of the rotating polygon mirror 316. Then the light beam of a specific frequency band impinging upon the optical fiber FB11 enters the optical fiber FB10, and as a result, only a laser beam La of the specific frequency band is emitted toward the optical fiber FB1.

Accordingly, when the rotating polygon mirror 316 rotates in the direction indicated by arrow R1 at a constant speed, the wavelength $\lambda$ of the light beam which reenters the optical fiber FB11 changes at a period with time. As a result, a laser beam La which is swept in its wavelength at a period is emitted from the light source unit 310 toward the optical fiber FB1.

The interference light detecting means 240 detects interference light beam L4 of the reflected light beam L3 and the reference light beam L2 which have been multiplexed by the multiplexing means 4 and the image obtaining means 250 detects the intensities of the reflected light beam L3 in positions in the direction of depth of the object Sb by carrying out frequency analysis on the interference light beam L4 detected by the interference light detecting means 240 and obtains a tomographic image of the object Sb. In this embodiment, an optical detector 40a which detects the intensity of the laser beam La branched from an fiber optic coupler 2 of the optical fiber FB1 and an optical detector 40b which detects the intensity of interference light beam L4 are provided and the interference light detecting means 40 has a function of adjusting the balance of the intensity of the interference light beam L4 on the basis of the output of the optical detector 40a.

Here, detection of the interference light beam L4 in the interference light detecting means 240 and image generation in the image obtaining means 250 will be described briefly. Note that a detailed description of these two points can be found in M. Takeda, "Optical Frequency Scanning Interference Microscopes", Optical Engineering Contact, Vol. 41, No. 7, pp. 426-432, 2003.

When the measuring light beam L1 is projected onto the object Sb, the reflected light L3 from each depth of the object Sb and the reference light L2 interfere with each other with various optical path length difference l. When the light intensity of the interference fringe at this time versus each optical path length difference is assumed to be S(l), the light intensity I(k) detected in the interference light detecting means 240 is expressed by the following formula.

$$I(k) = \int_0^\infty S(l)[1 + \cos(kl)]dl$$

wherein k represents the wave number and l represents the optical path length difference. The above formula may be considered to be given as an interferogram of a light frequency range having a wave number of ω/c(k=ω/c) as a variable. Accordingly, a tomographic image is generated by obtaining in the image obtaining means 250 information on the distance of the object Sb from the measurement initiating position and information on the intensity of reflection by carrying out frequency analysis by Fourier-transform on the spectral interference fringes detected by the interference light detecting means 240 and determining the intensity S(l) of the interference light beam L4.

In the optical tomography system 300, an optical probe 10 the same in arrangement as that employed in the system of FIG. 11 is employed and the operation is the same as that employed in the system of FIG. 11.

Figure 13:
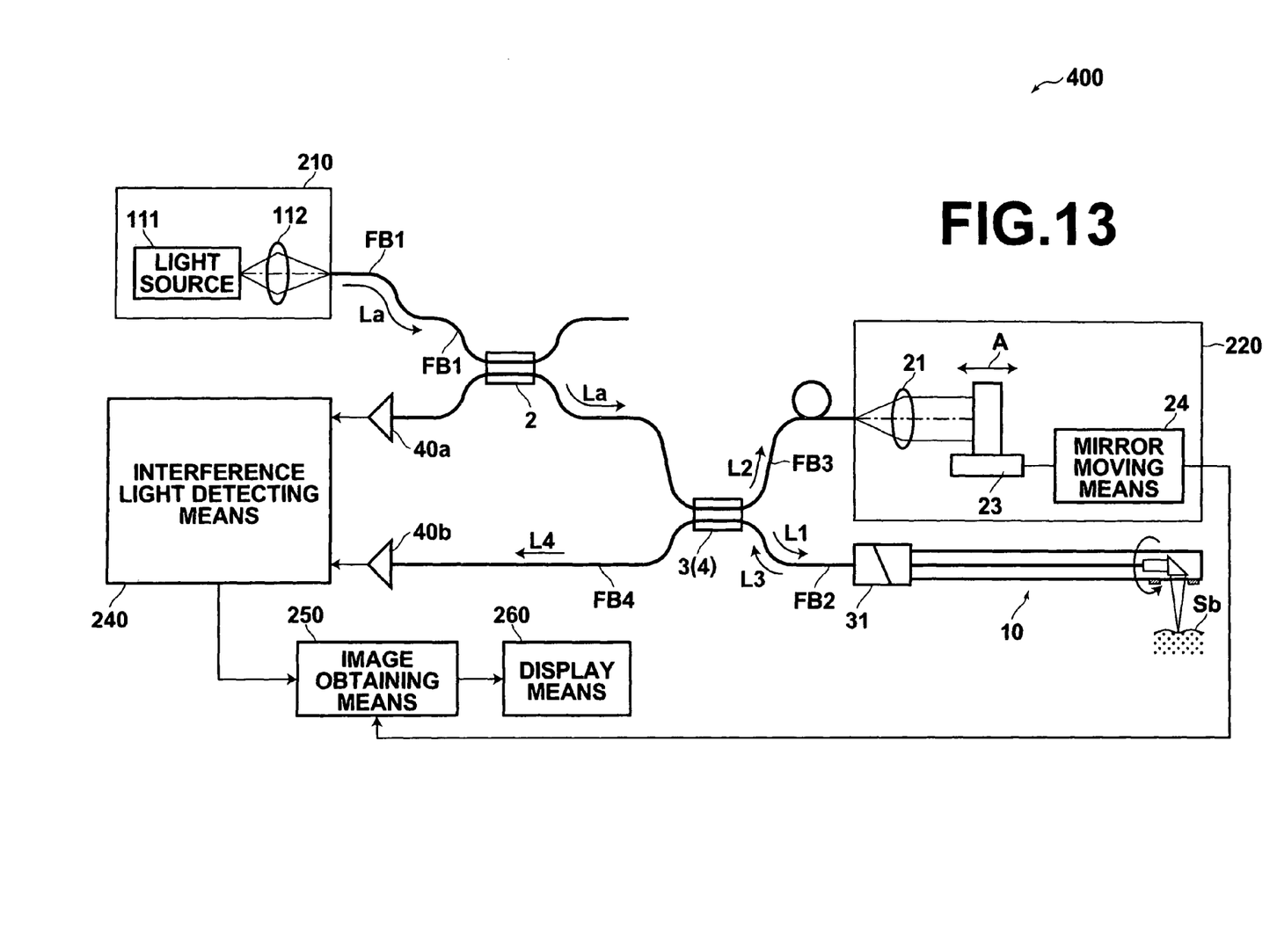
FIG. 13 is a schematic view showing an example of the optical tomography system by the TD-OCT measurement to which the optical probe of the present invention is applied.

Still another example of the optical tomography system to which the optical probes of the present invention are to be applied will be described, hereinbelow. The optical tomography system 400 shown in FIG. 13 is for obtaining a tomographic image of the object of measurement by measuring the TD-OCT and comprises a light source unit 210 provided with a light source 111 which emits laser light La and a light collecting lens, a light dividing means 2 which divides a laser light La emitted from the light source unit 210 and propagated through the optical fiber FB1, a light dividing means 3 which divides the laser light La passing therethrough into measuring light L1 and reference light L2, an optical path length adjusting means 220 which adjusts the optical path length of the reference light L2 divided by the light dividing means 3 and propagated through the optical fiber FB3, an optical probe 10 which projects onto the object S the measuring light L1 divided by the light dividing means 3 and propagated through the optical fiber FB2, a multiplexing means 4 (the light dividing means 3 doubles) which multiplexes the reflected light L3 from the object S when the measuring light L1 divided by the light dividing means is projected onto the object S and the reference light L2, and an interference light detecting means 240 which detects interference light L4 of the reflected light L3 and the reference light L2 which have been multiplexed by the multiplexing means 4.

The optical path length adjusting means 220 comprises a collimator lens 21 which makes parallel the reference light beam L2 radiated from the optical fiber FB3, a reflecting mirror 23 which is movable in the direction of arrow A to change the distance from the collimator lens 21, and a mirror moving means 24 which moves the reflecting mirror 23 and changes the optical path length of the reference light L2 in order to change the measuring position on the object Sb in the direction depth. A phase modulator 250 is disposed on the optical path of the reference light L2 (optical fiber FB3) to give a slight frequency shift to the reference light L2. The reference light L2 which has been changed in its optical path length and shifted in its frequency by the optical path length adjusting means 220 is guided to the multiplexing means 4.

Interference light detecting means 240 detects by, for instance, heterodyne detection the intensity of the interference light L4 propagating through the optical fiber FB2 from the multiplexing means 4. Specifically, when the sum of the total optical path length of the measuring light L1 and the total optical path length of the reflected light L3 is equal to the total optical path length of the reference light L2, a beat signal which varies in intensity at the difference frequency between the reference light L2 and the reflected light L3 is generated. As the optical path length is changed by the optical path length adjusting means 220, the measuring position (measuring depth) in the object S changes and the interference light detecting means 240 comes to detect beat signals in the measuring positions. Information on the measuring position is output from the optical path length adjusting means 220 to the image obtaining means.

On the basis of the beat signals detected by the interference light detecting means 240 and information on the measuring position in the mirror moving means 24, an optical tomographic image is generated by the image obtaining means 250. The generated tomographic image is displayed by the display system 260.

In the optical tomography system 400, an optical probe 10 the same in arrangement as that employed in the system of FIG. 11 is employed and the operation is the same as that employed in the system of FIG. 11.

Though the optical tomography systems 1, 300 and 400 in which the optical probe 10 is employed, the optical probes 100, 110, 120, 130 and 140 in accordance with previously described other embodiments of the present invention may be, of course, employed instead of the optical probe 10.

What is claimed is:

1. An optical probe comprising:
   a tubular outer envelope,
   a support member which extends in the longitudinal direction of the outer envelope inside the outer envelope,
   an optical fiber which extends in the longitudinal direction alongside and outside of the support member inside the outer envelope,
   a drive means which is connected to the base end portion of the support member and rotates the support member in the circumferential direction of the outer envelope,
   a light deflecting element which is rotated together with the support member and deflects light emitted from an end of the optical fiber in the circumferential direction of the outer envelope,
   a light collecting means which collects light emitted from an end of the optical fiber and converges it on a body-to-be-scanned disposed externally of the circumference of the outer envelope, and
   a light guide means which guides light reflected by the body-to-be-scanned to an end of the optical fiber to enter the optical fiber from the end,
   wherein the support member extends along a central axis that is offset from a center of rotation of the support member, and
   wherein the optical fiber extends along a central axis that is offset from the center of rotation of the support member in a direction opposite to a direction in which the central axis of the support member is offset.

2. An optical probe as defined in claim 1 in which the support member and the optical fiber are integrated so that the optical fiber rotates together with the support member.

3. An optical probe as defined in claim 2 in which the optical fiber is supported by the support member so that its central axis is deviated from the center of rotation of the support member, and
   a bearing portion which bears for rotation the rotating shaft of the support member is disposed in an end of the outer envelope.

4. An optical probe as defined in claim 3 in which the optical probe forms a front end portion of an endoscope.

5. An optical probe as defined in claim 2 in which the optical probe forms a front end portion of an endoscope.

6. An optical probe as defined in claim 1 in which the optical probe forms a front end portion of an endoscope.

7. An optical tomography system for obtaining a tomographic image of an object to be measured comprising:
- a light source unit which emits light,
- a light dividing means which divides light emitted from the light source unit into measuring light and reference light,
- a projecting optical system which projects the measuring light onto the object,
- a multiplexing means which multiplexes the reflected light from the object when the measuring light is projected onto the object and the reference light,
- an interference light detecting means which detects interference light of the reflected light and the reference light which have been multiplexed by the multiplexing means, and
- a tomographic image obtaining means which detects intensities of the interference light in positions in the direction of depth of the object on the basis of the frequency and intensity of the detected interference light and obtains a tomographic image of the object on the basis of the intensity of the reflected light in each position of the depth, and
- wherein the projecting optical system includes the optical probe as set forth in claim 1.

8. An optical tomography system for obtaining a tomographic image of an object to be measured comprising
- a light source unit which emits light,
- a light dividing means which divides light emitted from the light source unit into measuring light and reference light,
- a projecting optical system which projects the measuring light onto the object,
- a multiplexing means which multiplexes the reflected light from the object when the measuring light is projected onto the object and the reference light,
- an interference light detecting means which detects interference light of the reflected light and the reference light which have been multiplexed by the multiplexing means, and
- a tomographic image obtaining means which detects intensities of the interference light in positions in the direction of depth of the object on the basis of the frequency and intensity of the detected interference light and obtains a tomographic image of the object on the basis of the intensity of the reflected light in each position of the depth,
- wherein the projecting optical system includes the optical probe as set forth in claim 2.

9. An optical tomography system for obtaining a tomographic image of an object to be measured comprising
- a light source unit which emits light,
- a light dividing means which divides light emitted from the light source unit into measuring light and reference light,
- a projecting optical system which projects the measuring light onto the object,
- a multiplexing means which multiplexes the reflected light from the object when the measuring light is projected onto the object and the reference light,
- an interference light detecting means which detects interference light of the reflected light and the reference light which have been multiplexed by the multiplexing means, and
- a tomographic image obtaining means which detects intensities of the interference light in positions in the direction of depth of the object on the basis of the frequency and intensity of the detected interference light and obtains a tomographic image of the object on the basis of the intensity of the reflected light in each position of the depth,
- wherein the projecting optical system includes the optical probe as set forth in claim 3.

10. An optical tomography system for obtaining a tomographic image of an object to be measured comprising
- a light source unit which emits light,
- a light dividing means which divides light emitted from the light source unit into measuring light and reference light,
- a projecting optical system which projects the measuring light onto the object,
- a multiplexing means which multiplexes the reflected light from the object when the measuring light is projected onto the object and the reference light,
- an interference light detecting means which detects interference light of the reflected light and the reference light which have been multiplexed by the multiplexing means, and
- a tomographic image obtaining means which detects intensities of the interference light in positions in the direction of depth of the object on the basis of the frequency and intensity of the detected interference light and obtains a tomographic image of the object on the basis of the intensity of the reflected light in each position of the depth,
- wherein the projecting optical system includes the optical probe as set forth in claim 4.

* * * * *